US010818073B2

(12) United States Patent
Mistretta et al.

(10) Patent No.: US 10,818,073 B2
(45) Date of Patent: Oct. 27, 2020

(54) SYSTEM AND METHOD FOR TIME-RESOLVED, THREE-DIMENSIONAL ANGIOGRAPHY WITH FLOW INFORMATION

(71) Applicant: Wisconsin Alumni Research Foundation, Madison, WI (US)

(72) Inventors: Charles A. Mistretta, Madison, WI (US); Charles M. Strother, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 868 days.

(21) Appl. No.: 14/643,853

(22) Filed: Mar. 10, 2015

(65) Prior Publication Data
US 2016/0267704 A1 Sep. 15, 2016

(51) Int. Cl.
*G06T 15/08* (2011.01)
*A61B 6/00* (2006.01)
(Continued)

(52) U.S. Cl.
CPC .......... *G06T 15/08* (2013.01); *A61B 5/0263* (2013.01); *A61B 5/0275* (2013.01); *A61B 6/4441* (2013.01); *A61B 6/463* (2013.01); *A61B 6/466* (2013.01); *A61B 6/481* (2013.01); *A61B 6/486* (2013.01); *A61B 6/504* (2013.01); *A61B 6/507* (2013.01); *A61B 6/5217* (2013.01); *A61B 6/5235* (2013.01); *G06T 7/0014* (2013.01); *G06T 7/248* (2017.01); *G06T 2207/10076* (2013.01); *G06T 2207/10116* (2013.01); *G06T 2207/30104* (2013.01)

(58) Field of Classification Search
CPC .......... G06T 15/08; G06T 2207/10076; G06T 2207/10116; G06T 2207/30104; G06T 7/0014; G06T 7/248
See application file for complete search history.

(56) References Cited

U.S. PATENT DOCUMENTS 8,643,642 B2 2/2014 Mistretta et al.
8,768,031 B2 7/2014 Mistretta et al.
(Continued)

FOREIGN PATENT DOCUMENTS

WO 2012011014 A1 1/2012

OTHER PUBLICATIONS

Huang et al., "On Concise 3-D Simple Point Characterizations: A Marching Cubes Paradigm", IEEE Transactions on Medical Imaging, vol. 28, No. 1, Jan. 2009, pp. 43-51.*
(Continued)

*Primary Examiner* — Katherine L Fernandez
(74) *Attorney, Agent, or Firm* — Quarles & Brady LLP (57) ABSTRACT

A system and method are provided for generating time resolved series of angiographic volume data having flow information integrated therewith. The method includes generating a series of 3D time-resolved vascular volumes from time resolved x-ray projection data and calculating blood velocity in the vascular volumes x-ray projection data to determine a rate of change of calculated contrast material arrival time at positions along the vascular volumes. The method also includes displaying the 3D time-resolved vascular volumes with a graphical indication of blood velocity in the vascular volumes.

11 Claims, 8 Drawing Sheets

(51) Int. Cl.
*A61B 5/0275* (2006.01)
*A61B 5/026* (2006.01)
*G06T 7/246* (2017.01)
*G06T 7/00* (2017.01)

(56) References Cited

U.S. PATENT DOCUMENTS

| | | | | |
|---|---|---|---|---|
| 10,134,144 | B2* | 11/2018 | Mistretta | G06T 7/246 |
| 2004/0247167 | A1* | 12/2004 | Bueno | G06T 1/20 |
| | | | | 382/132 |
| 2009/0016587 | A1 | 1/2009 | Strobel et al. | |
| 2010/0053209 | A1 | 3/2010 | Rauch et al. | |
| 2010/0067767 | A1 | 3/2010 | Arakita et al. | |
| 2011/0037761 | A1* | 2/2011 | Mistretta | A61B 6/4441 |
| | | | | 345/419 |
| 2011/0150309 | A1* | 6/2011 | Barfett | G06T 7/33 |
| | | | | 382/131 |
| 2011/0213244 | A1* | 9/2011 | Frinking | A61B 5/055 |
| | | | | 600/431 |
| 2011/0235885 | A1 | 9/2011 | Rauch et al. | |
| 2012/0114217 | A1 | 5/2012 | Mistretta et al. | |
| 2013/0046176 | A1* | 2/2013 | Mistretta | A61B 6/032 |
| | | | | 600/431 |
| 2013/0345559 | A1* | 12/2013 | Haemmerich | A61B 5/0275 |
| | | | | 600/431 |
| 2014/0094680 | A1 | 4/2014 | Kowarschik et al. | |
| 2014/0153690 | A1* | 6/2014 | Claus | A61B 6/025 |
| | | | | 378/9 |

OTHER PUBLICATIONS

Blackshear, et al., Carotid Artery Velocity Patterns in Normal and Stenotic Vessels, Stroke, 1980, 11(1):67-71.
Canny, A Computational Approach to Edge Detection, IEEE Transactions on Pattern Analysis and Machine Intelligence, 1986, PAMI-8(6):679-698.
Chaudhury, et al., Fast O(1) Bilateral Filtering Using Trigonometric Range Kernels, IEEE Trans. Image Proc., 2011, 20(11):1-16.
Donoho, De-Noising by Soft-Thresholding, IEEE Transactions on Information Theory, 1995, 41(3):613-627.
Fahrig, et al., Use of a C-Arm System to Generate True Three-Dimensional Computed Rotational Angiograms: Preliminary in Vitro and in Vivo Results, American Journal of Neuroradiology, 1997, 18:1507-1514.
Hermus, et al., Quantitative Analysis of Artifacts in 4D DSA: The Relative Contributions of Beam Hardening and Scatter to Vessel Dropout Behind Highly Attenuating Structures, Proc. of SPIE, 2014, vol. 9033, pp. 90332G-1 thru 90332G-12.
Hinkmann, et al., Ultra-Fast Carotid CT-Angiography: Low Versus Standard Volume Contrast Material Protocol for a 128-Slice CT-System, Investigative Radiology, 2009, 44(5):257-264.
Keith, et al. Motion Adaptive Hypr: An Algorithm for Dynamic Imaging Applications, Proc. Intl. Soc. Mag. Reson. Med., 2009, 17:562.
Mistretta, et al., Highly Constrained Backprojection for Time-Resolved MRI, Magnetic Resonance in Medicine, 2006, 55:30-40.
Palagyi, et al., A Sequential 3D Thinning Algorithm and Its Medical Applications, Biennial International Conference on Information Processing in Medical Imaging, 2001, pp. 409-415.
Pereira, et al., Quantification of Internal Carotid Artery Flow With Digital Subtraction Angiography: Validation of an Optical Flow Approach with Doppler Ultrasound, American Journal of Neuroradiology, 2014, 35:156-163.
Shpilfoygel, et al., X-Ray Videodensitometric Methods for Blood Flow and Velocity Measurement: A Critical Review of Literature, Medical Physics, 2000, 27(9):2008-2023.
Wagner, et al., Directional Denoising and Line Enhancement for Device Segmentation in Real Time Fluoroscopic Imaging, Proc. of SPIE, 2015, vol. 9413, pp. 94132C-1 thru 94132C-7.
PCT International Search Report and Written Opinion, PCT/US2016/021455, dated May 23, 2016.
Bonnefous, O., et al. "Quantification of arterial flow using digital subtraction angiography." Medical physics 39.10 (2012): 6264-6275.
Lin, C. J., et al. "In-room assessment of intravascular velocity from time-resolved rotational angiography in patients with arteriovenous malformation: a pilot study." Journal of neurointerventional surgery 10.6 (2018): 580-586.

* cited by examiner

SYSTEM AND METHOD FOR TIME-RESOLVED, THREE-DIMENSIONAL ANGIOGRAPHY WITH FLOW INFORMATION

STATEMENT REGARDING FEDERALLY SPONSORED RESEARCH OR DEVELOPMENT

This invention was made with government support under HL116567 awarded by the National Institutes of Health. The government has certain rights in the invention.

CROSS-REFERENCE TO RELATED APPLICATIONS

N/A

BACKGROUND

The present disclosure is directed to angiography and, in particular, the disclosure relates to a system and method for producing time-resolved, three-dimensional (3D) angiographic images, as referred to as four dimensional (4D) angiographic images including flow information generated from x-ray data.

Since the introduction of angiography beginning with the direct carotid artery punctures of Moniz in 1927, there have been ongoing attempts to develop angiographic techniques that provide diagnostic images of the vasculature, while simultaneously reducing the invasiveness associated with the procedure. In the late 1970's, a technique known as digital subtraction angiography (DSA) was developed based on real-time digital processing equipment. Due to steady advancements in both hardware and software, DSA can now provide depictions of the vasculature in both 2D and rotational 3D formats. Three-dimensional digital subtraction angiography (3D-DSA) has become an important component in the diagnosis and management of people with a large variety of central nervous system vascular diseases.

In recent years competition for traditional DSA has emerged in the form of computed tomography angiography (CTA) and magnetic resonance angiography (MRA). CTA provides higher spatial resolution, but is not time-resolved unless the imaging volume is severely limited. The images are not isotropic and secondary reconstruction yields degraded spatial resolution. CTA is also limited as a stand-alone diagnostic modality by artifacts caused by bone at the skull base and the contamination of arterial images with opacified venous structures. Further, CTA provides no functionality for guiding or monitoring minimally-invasive endovascular interventions. Significant advances have been made in both the spatial and the temporal resolution qualities of MRA. Currently, gadolinium-enhanced time-resolved MRA (TRICKS) is widely viewed as a dominant clinical standard for time-resolved MRA. TRICKS enables voxel sizes of about 10 mm$^3$ and a temporal resolution of approximately 10 seconds. Advancements such as HYBRID highly constrained projection reconstruction (HYPR) MRA techniques, which violate the Nyquist theorem by factors approaching 1000, can provide images with sub-millimeter isotropic resolution at frame times just under 1 second. Nonetheless, the spatial and temporal resolution of MRA are not adequate for all imaging situations and its costs are considerable. Furthermore, the spatial and temporal resolution is substantially below other methods, such as DSA.

The recently-introduced, four-dimensional (4D) DSA techniques can use rotational DSA C-arm imaging systems controlled with respect to a particular injection timing so that there is time dependence in the acquired reconstructed 4D volumes. As described in U.S. Pat. No. 8,643,642, which is incorporated herein by reference, a 3D DSA volume can be used as a constraining volume to generate a new 3D volume contains the temporal information of each projection. As in 3D DSA, a mask rotation without contrast is followed by a second rotation in which contrast is injected. The process creates a series of time resolved 3D angiographic volumes that can be updated, for example, every ⅓₀ of a second.

Thus, the above-described systems and methods have improved over time and, thereby, provided clinicians with an improving ability to visualize the anatomy of the vessels being studied. Of course, vessels are dynamic and functional structures and the specifics of the anatomy is used by the clinician to deduce information about the dynamic and functional nature of the vessels. Put another way, with ever increasing spatial and temporal resolution, the clinician has been provided with clearer and more accurate information about the geometry (i.e., anatomy) of the vessels. Unfortunately, the equally important dynamics of blood flow through the vasculature still depends upon the qualitative assessment gained from visualization of a contrast bolus as it passes through the vessels. As such, while the deductions made by the clinician about the structural dynamics and function of the vessel (i.e. anatomy) have correspondingly improved, even the best deductions about the circulatory dynamics (e.g. blood flow and velocity) are still qualitative and thus inherently limited.

Therefore, it would be desirable to have a system and method for providing information about the function or dynamic performance of the vasculature as well as its anatomy to a clinician performing an angiographic study.

SUMMARY

The present disclosure overcomes the aforementioned drawbacks by providing a system and method for integrating functional and/or dynamic flow information with high-quality anatomical angiographic images. In particular, a system and method is provided that can integrate flow information with a time-resolved angiographic study, including 4D DSA studies. In one configuration, velocity information or flow information is coupled with 4D DSA images to provide time-resolved, anatomical angiographic images that include flow or velocity and velocity-derived information.

In accordance with one aspect of the disclosure, a system is provided for generating time resolved series of angiographic volume data having velocity or velocity-derived information integrated therewith. The system includes an image processing system configured to receive angiographic volume data acquired from a subject having received a dose of a contrast agent using an imaging system, process the angiographic volume data to generate angiographic volume images, and process the angiographic volume data to derive flow information associated with vessels in the angiographic volume images. The system also includes a display configured to display the angiographic volume images of the subject including the flow information coupled with at least a portion of the vessels in the angiographic volume images.

In accordance with another aspect of the disclosure, a method is provided for generating time resolved series of angiographic volume data having flow information integrated therewith. The method includes generating a series of 3D time-resolved vascular volumes from time resolved x-ray projection data and calculating blood velocity in the vascular volumes x-ray projection data to determine a rate of change of calculated contrast material arrival time at positions along the vascular volumes. The method further includes displaying the 3D time-resolved vascular volumes with a graphical indication of blood velocity in the vascular volumes.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
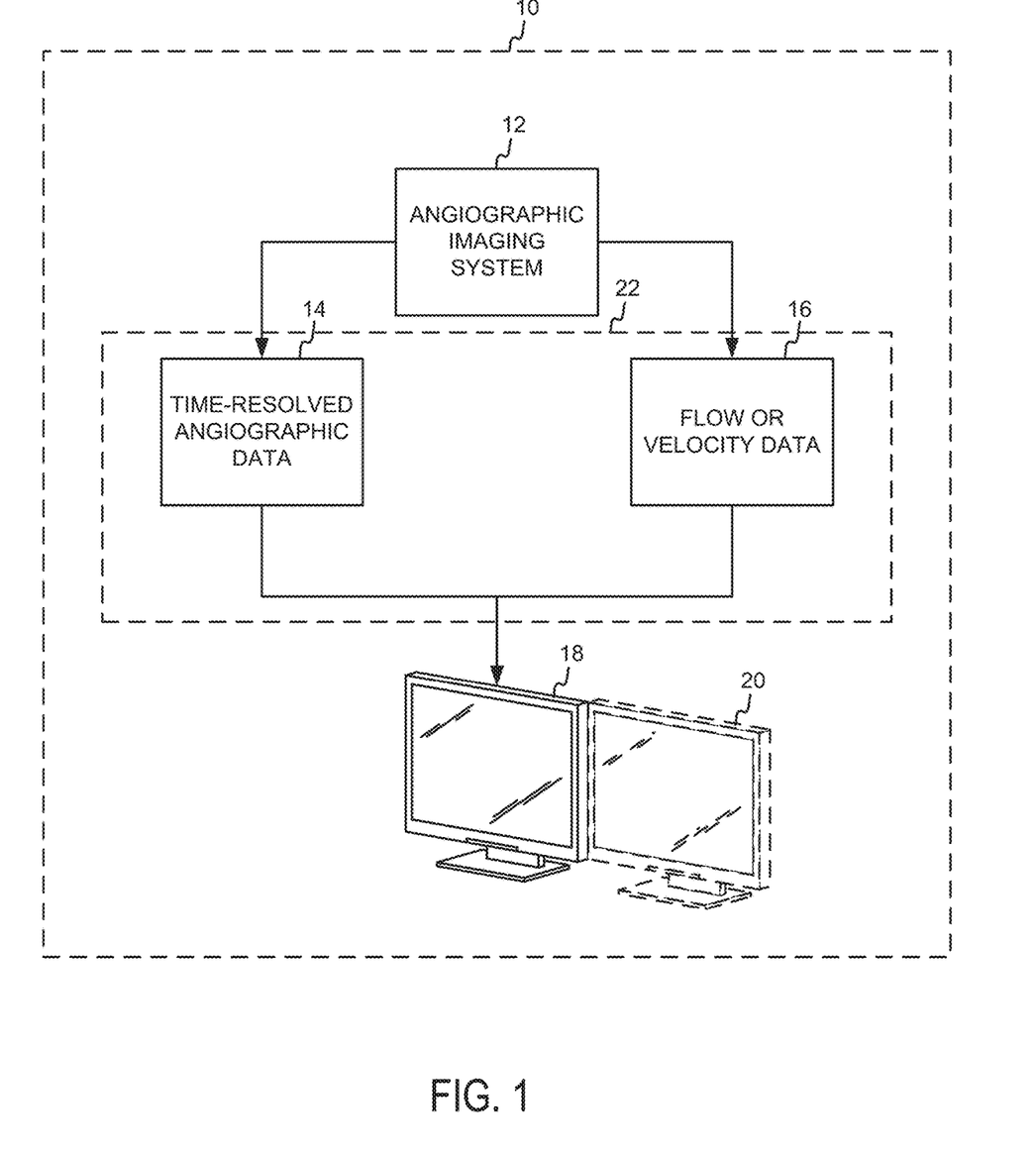
FIG. 1 is a block diagraph of a system for creating time-resolved, three-dimensional (3D), angiographic images having flow or velocity information in accordance with the present disclosure.

Referring to FIG. 1, a system 10 is illustrated for creating time-resolved angiographic images having flow or velocity information. In particular, the system 10 includes an angiographic imaging system 12. As will be described, the angiographic imaging system 12 can be used to acquire data, which can be conceptualized as including time-resolved angiographic data 14 and flow or velocity data 16. The time-resolved angiographic data 14 and flow or velocity data 16 can be processed and provided to a clinician via a display 18. As will be further described, the information may be provided to the clinician using multiple displays including a first display 18 and a secondary display 20 or multiple additional displays. As will also be described, the process of deriving velocity or flow data can be performed partially or in whole using an image processing system, which may include a graphics processing unit (GPU) or other processor, including a central processing unit (CPU).

Figure 2A:
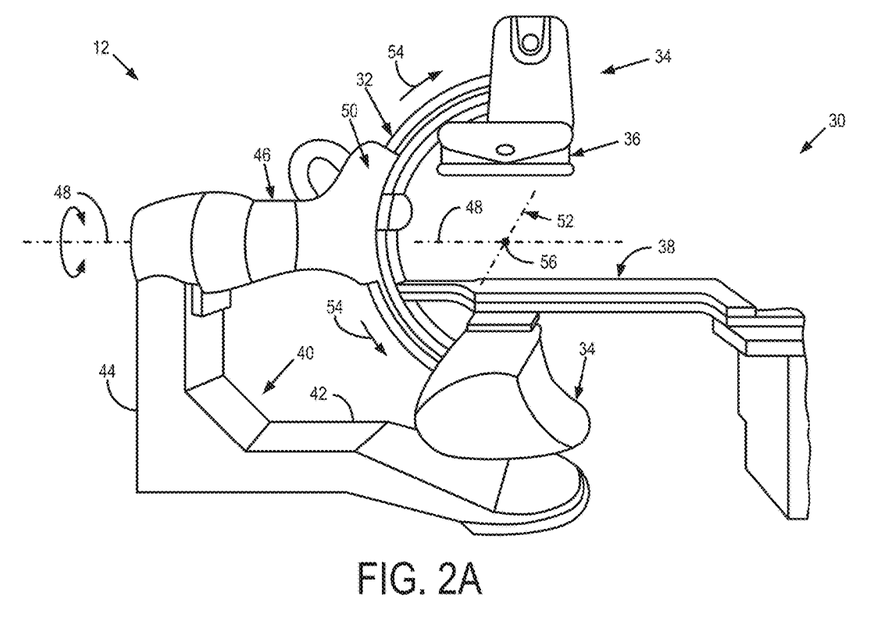
FIG. 2A is a perspective view of an example of an x-ray imaging system that can be used in accordance with the present disclosure to acquire angiographic data.
Figure 2B:
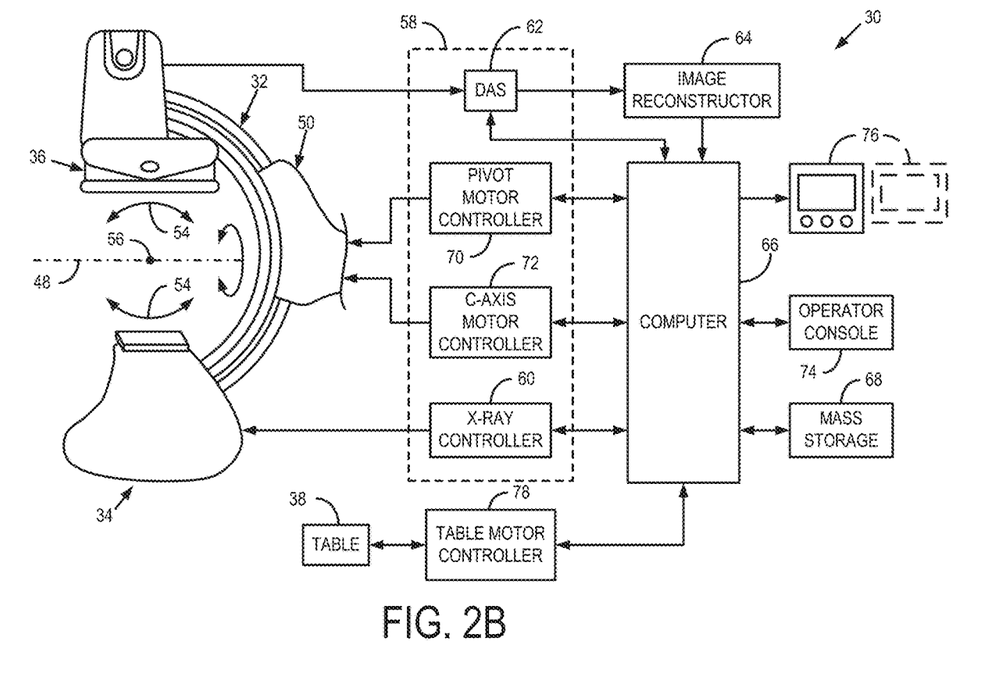
FIG. 2B is a block diagram of the system of FIG. 2A

Referring now to FIGS. 2A and 2B, an example of the angiographic imaging system 12 may include an x-ray imaging system 30. The x-ray imaging system 30 is illustrated as a so-called "C-arm" imaging system; however, other geometries may be used to acquired x-ray angiographic images. For example, any of a variety of x-ray imaging systems capable of acquiring data to create a 4D-DSA image may be used, including systems that acquire time-resolved 2D images using a single plane x-ray system.

The imaging system 30, as illustrated, may be generally designed for use in connection with interventional procedures. The imaging system 30 is characterized by a gantry 32 forming a C-arm that carries an x-ray source assembly 34 on one of its ends and an x-ray detector array assembly 36 at its other end. The gantry 32 enables the x-ray source assembly 34 and detector array assembly 36 to be oriented in different positions and angles around a patient disposed on a table 38, while enabling a physician access to the patient.

The gantry includes a support base 40, which may include an L-shaped pedestal that has a horizontal leg 42 that extends beneath the table 38 and a vertical leg 44 that extends upward at the end of the horizontal leg 42 that is spaced from of the table 38. A support arm 46 is rotatably fastened to the upper end of vertical leg 44 for rotation about a horizontal pivot axis 48. The pivot axis 48 is aligned with the centerline of the table 38 and the support arm 46 extends radially outward from the pivot axis 48 to support a drive assembly 50 on its outer end. The C-arm gantry 32 is slidably fastened to the drive assembly 50 and is coupled to a drive motor (not shown) that slides the C-arm gantry 32 to revolve it about a C-axis 52, as indicated by arrows 54. The pivot axis 48 and C-axis 52 intersect each other at an isocenter 56 that is located above the table 408 and they are perpendicular to each other.

The x-ray source assembly 34 is mounted to one end of the C-arm gantry 32 and the detector array assembly 36 is mounted to its other end. As will be discussed in more detail below, the x-ray source assembly 34 includes an x-ray source (not shown) that emits a beam of x-rays, which are directed at the detector array assembly 36. Both assemblies 34 and 36 extend radially inward to the pivot axis 38 such that the center ray of this cone beam passes through the system isocenter 56. The center ray of the x-ray beam can, thus, be rotated about the system isocenter 56 around either the pivot axis 38, the C-axis 52, or both during the acquisition of x-ray attenuation data from a subject placed on the table 38.

As mentioned above, the x-ray source assembly 34 contains an x-ray source that emits a beam of x-rays when energized. The center ray passes through the system isocenter 56 and impinges on a two-dimensional flat panel digital detector housed in the detector assembly 36. Each detector element produces an electrical signal that represents the intensity of an impinging x-ray and, hence, the attenuation of the x-ray as it passes through the patient. During a scan, the x-ray source and detector array are rotated about the system isocenter 56 to acquire x-ray attenuation projection data from different angles. By way of example, the detector array is able to acquire thirty projections, or views, per second. Generally, the numbers of projections acquired per second is the limiting factor that determines how many views can be acquired for a prescribed scan path and speed. Accordingly, as will be described, this system or others can be used to acquire data that can be used to crate 4D DSA image data sets that may provide 3D angiographic volumes at the rate of, for example, 30 per second. As will be further described, such 4D DSA images may be augmented with flow or velocity information.

Referring particularly to FIG. 2B, the rotation of the assemblies 34 and 36 and the operation of the x-ray source are governed by a control system 58 of the imaging system 30. The control system 58 includes an x-ray controller 60 that provides power and timing signals to the x-ray source. A data acquisition system (DAS) 62 in the control system 58 samples data from detector elements in the detector array assembly 36 and passes the data to an image reconstructor 64. The image reconstructor 64, receives digitized x-ray data from the DAS 62 and performs image reconstruction. The image reconstructed by the image reconstructor 64 is applied as an input to a computer 66, which stores the image in a mass storage device 68 or processes the image further.

The control system 58 also includes pivot motor controller 70 and a C-axis motor controller 72. In response to motion commands from the computer 66, the motor controllers 70 and 72 provide power to motors in the imaging system 30 that produce the rotations about the pivot axis 38 and C-axis 52, respectively. A program executed by the computer 66 generates motion commands to the motor controllers 70 and 72 to move the assemblies 34 and 36 in a prescribed scan path.

The computer 66 also receives commands and scanning parameters from an operator via a console 74 that has a keyboard and other manually operable controls. An associated display 76 or displays allows the operator to observe the reconstructed image and other data from the computer 66. The operator supplied commands are used by the computer 66 under the direction of stored programs to provide control signals and information to the DAS 62, the x-ray controller 60, and the motor controllers 70 and 72. In addition, the computer 66 operates a table motor controller 78, which controls the patient table 408 to position the patient with respect to the system isocenter 56.

Figure 3:
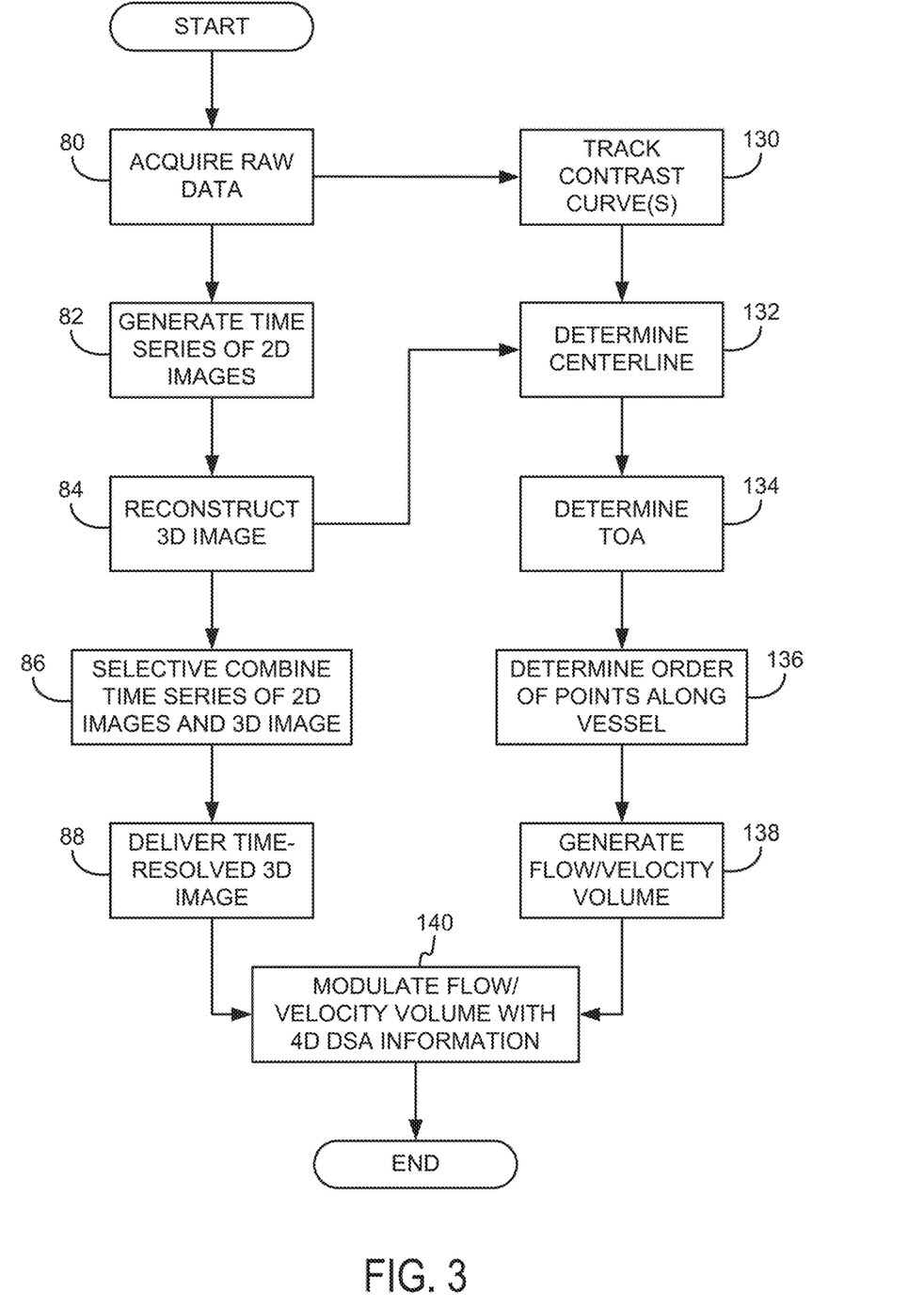
FIG. 3 is a flow chart setting forth examples of steps for producing a time-resolved 3D image or 4D DSA dataset from x-ray data.

The above-described system can be used to acquire raw angiographic data that can then be processed to generate a time-resolved 3D angiographic image in the form of a 4D DSA image. Referring to FIG. 3, a process for creating a 4D DSA image begins at process block 80 with the acquisition of image data from a region-of-interest in a subject using a medical imaging system, such as a CT system or a single-plane, biplane, or rotational x-ray systems. At process block 82, a time-series of 2D images is generated from at least a portion of the acquired image data. While the time-series of 2D images can have a high temporal and spatial resolution and may include images acquired at different angles around the subject, it generally cannot provide a sophisticated 3D depiction of the subject. At process block 84, a 3D image of the subject is reconstructed from the acquired image data. Though individual projections used to reconstruct this 3D image may themselves convey some degree of temporal information, the reconstructed 3D image itself is substantially free of temporal resolution. For brevity, the 3D image substantially without temporal resolution and the time-series of 2D images may simply be referred to as the "3D image" and "2D images," respectively.

At process block 86, the time-series of 2D images and the static 3D image are selectively combined so that the temporal information included in the 2D images is imparted into the 3D image. This results in the production of a time-resolved 3D image of the subject with high temporal and spatial resolution. While the selective combination process varies based on the medical imaging system used and the nature of the acquired image data, it generally involves the steps of (1) registering the 2D images to the 3D image, (2) projecting the attenuation value of the pixels in the 2D images into the 3D image, and (3) weighting the 3D image with the projected values for each individual frame of the time-series of 2D images. It is contemplated that the temporal weighting in step (3) generally involves multiplying the projected pixel values with the 3D image. These three steps, which can be referred to as "multiplicative projection processing" (MPP), may be accompanied by additional steps to improve image quality or reduce the prevalence of errors and artifacts. For example, the intensity values of pixels and voxels in the 2D images and 3D image produced at process blocks 82 and 84 may quantify an x-ray attenuation level at a given location in the subject. These attenuation levels may not be preserved when multiplying the 3D image with projected pixel values. Accordingly, more accurate indications of the attenuation levels may be restored using the intensity value at each voxel in the time-resolved 3D image, for example, by taking the n-th root, if (n−1) different sets of 2D images are used, to weight the 3D image.

The 2D images and 3D image produced at process blocks 82 and 84, respectively, can be produced using DSA techniques. That is, 2D images depicting the subject's vasculature can be produced by reconstructing image data acquired as a bolus of contrast passes through the vasculature and subtracting out a pre-contrast, or "mask," image acquired before the administration of contrast agent. Likewise, a 3D image of the same vascular structures can be produced by reconstructing image data acquired as contrast agent occupies the vasculature and subtracting out a mask image to remove signal associated with non-vascular structures. The time-resolved 3D image produced by combining the DSA images depicts the subject's vascular structures with both excellent spatial and excellent temporal resolution and may thus be referred to as a 4D-DSA image. As used herein, this time-resolved 3D image may also be referred to as a 4D image, a 4D angiographic image, or a 4D DSA image. The 4D-DSA images can be displayed as "pure" arterial, pure venous, or composite arterial and venous images and can be fully rotated during each state of the filling of the vasculature, thereby enabling greatly simplified interpretation of vascular dynamics. The spatial resolution of these 4D-DSA images may be on the order of $512^3$ pixels at about 30 frames per second. This represents an increase over traditional 3D-DSA frame rates by a factor between 150 and 600, without any significant image quality penalty being incurred. Further discussion of 4D DSA techniques may be found in U.S. Pat. No. 6,643,642, which is incorporated herein by reference in its entirety. Also, U.S. Pat. No. 8,768,031 is incorporated herein by reference, which extends the 4D DSA imaging process to use time-independent 3D rotational DSA volumes. Furthermore, US Published Patent Application US2013/0046176, which describes the use of dual-energy x-ray imaging with 4D DSA, is incorporated herein by reference.

Figure 4:
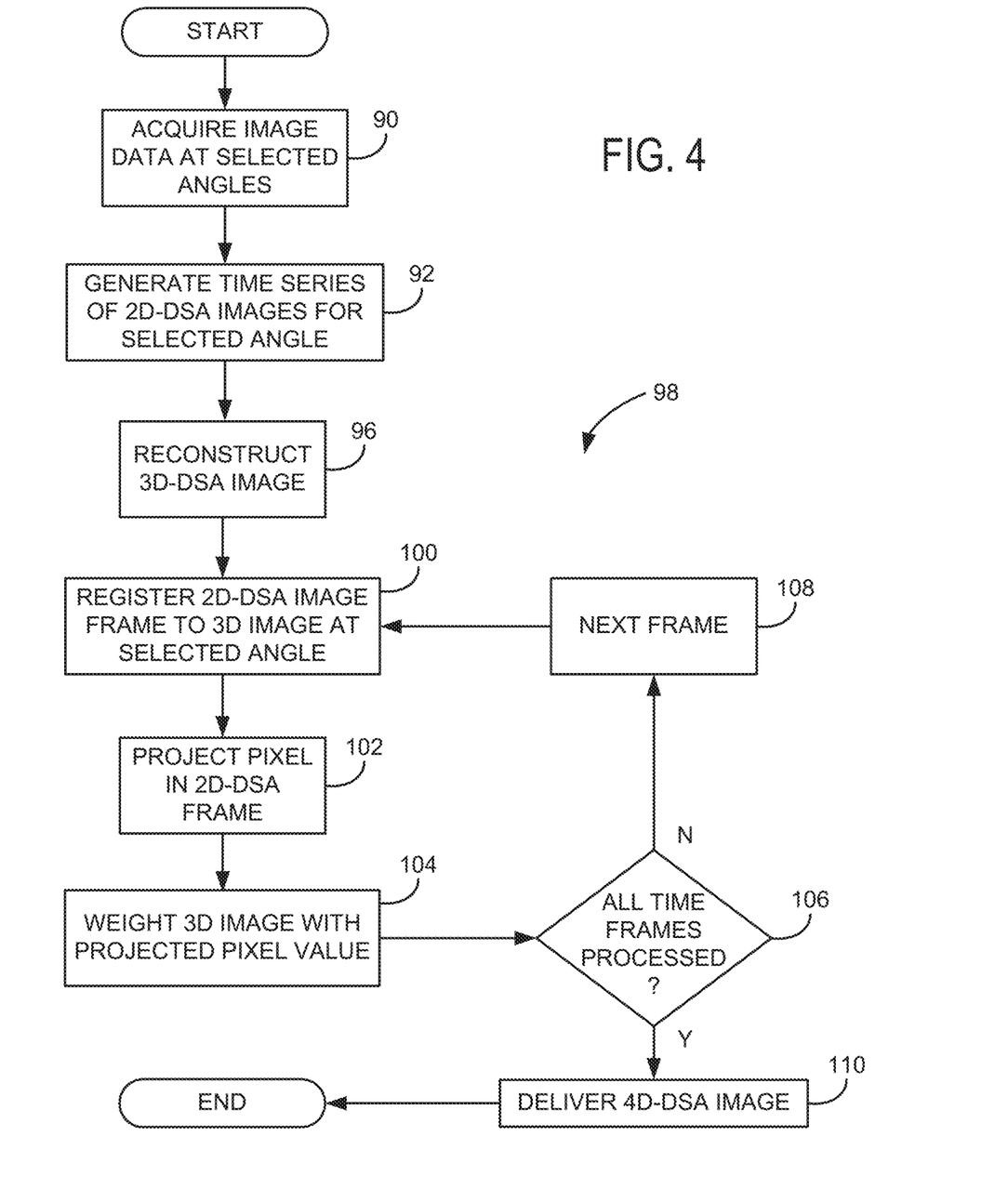
FIG. 4 is a flow chart setting forth further examples of steps for producing a time-resolved 3D image or 4D DSA dataset from x-ray data.

Referring to FIG. 4, a more specific implementation of the above-described process can be employed to produce a 4D-DSA image of a subject using a single-plane x-ray system in combination with a rotational x-ray system or CT system. In this case, the process begins at process block 90, when time-resolved image data from a ROI in the subject is acquired using the single-plane system following the administration of a contrast agent to the subject. Using the above-discussed DSA techniques, a time-series of 2D-DSA images at selected angles about the ROI is generated at process block 92. These 2D-DSA images depict the contrast agent passing through and enhancing arterial structures in the ROI. The 2D-DSA images are substantially free of signal from non-vascular structures, as well as signal from venous structures can be excluded due to the high temporal resolution of the 2D acquisition. A 3D-DSA image is reconstructed at process block 96 from the acquired image data. Specifically, the projections acquired at process block 90 may be log subtracted from those acquired in a non-contrast mask sweep. Typically, vascular structures in the 3D-DSA image are substantially opacified due to the use of contrast agent and the time necessary for data acquisition.

Figure 5:
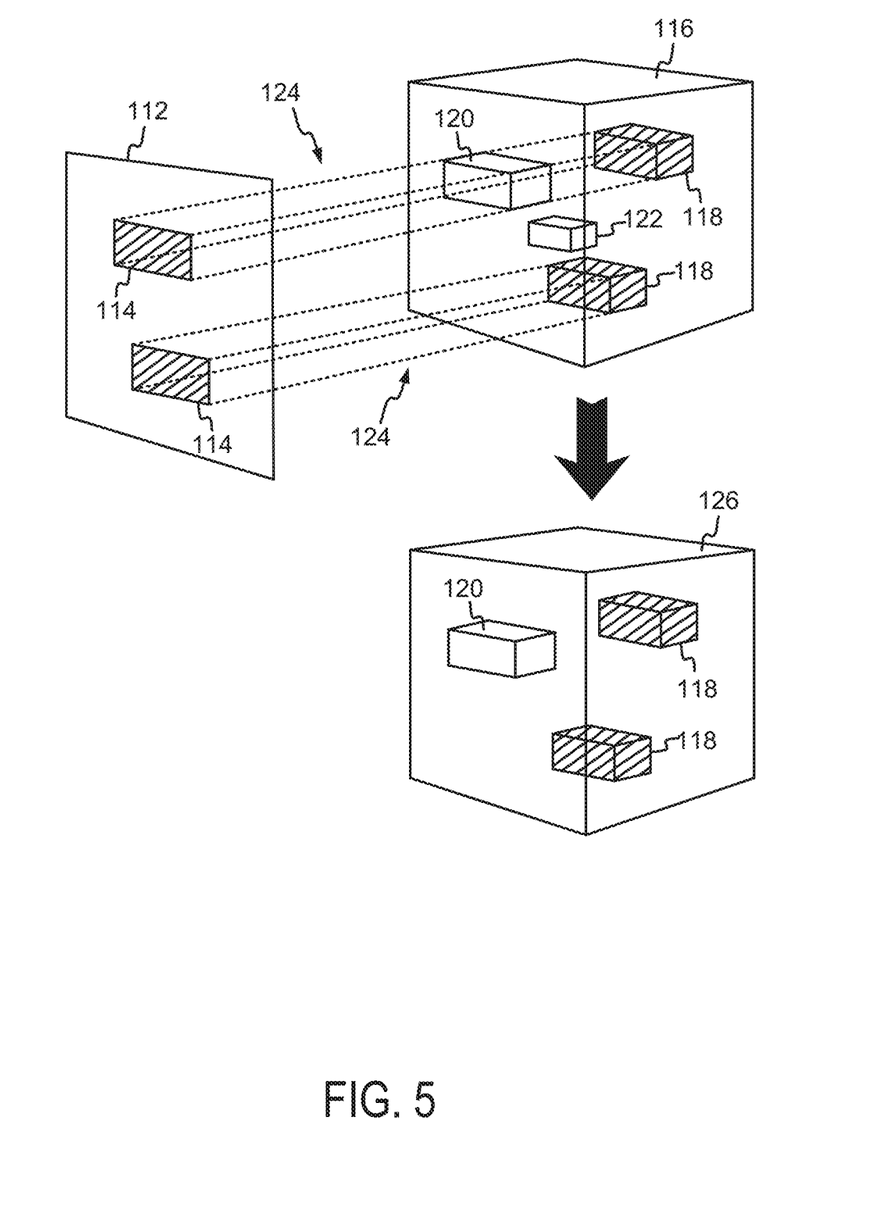
FIG. 5 is a graphic depiction of selection combination of a 3D image with a 2D DSA image frame to produce 4D DSA data.

Referring now to FIGS. 4 and 5, the images produced thus far can be selectively combined with the steps indicated generally at 98 to produce a 4D-DSA image with the detailed 3D resolution of the 3D-DSA image and the temporal resolution of the time-series of 2D-DSA images. In the exemplary depiction of the selective combination process provided in FIG. 5, a single frame of the time-series of 2D-DSA images 112 includes two image regions having arterial signal 114, while the 3D-DSA image 116 includes both arterial signal 118 and venous signal 120 and 122. At process block 100 of FIG. 4, a frame of the 2D-DSA image 112 is registered to the 3D-DSA image 116 at the selected angle and, at process block 102, the values of the pixels in the 2D-DSA frame are projected along a line passing through each respective pixel in a direction perpendicular to the plane of the 2D-DSA frame. The projection of pixels with arterial signal 114 into the 3D-DSA image is indicated generally at 124. For simplicity, the projection of pixels in the 2D-DSA frame with no contrast is not shown. At process block 104 of FIG. 4, the 3D-DSA image 116 is weighted by the values projected from the 2D-DSA frame 112 to produce the 4D-DSA image 126. This may include multiplying the projected values with the voxels of the 3D image that they intersect. The weighting process results in the preservation of the arterial signal 118 and the exclusion, or "zeroing-out," of undesired venous signal 122 in the 4D-DSA image. In addition, the intensity value of the arterial signal 114 in the 2D-DSA frame is imparted into the 3D arterial signal volume 118, thereby allowing the changes in arterial signal over time captured by the 2D-DSA images to be characterized in the 4D-DSA image. At decision block 106 of FIG. 4, if all of the frames have yet to be processed, the process moves to the next frame of the time-series of 2D-DSA images at process block 108 and repeats the selective combination process generally designated at 98. This cycle continues until, at decision block 106, it is determined that a 4D-DSA image has been generated for all relevant time frames. The 4D-DSA image can thus be delivered at process block 110.

The venous signal 120 preserved in the 4D-DSA image 126 illustrates a potential challenge when generating 4D images using only a single time-series of 2D images acquired at a single angle. That is, signal from desired structures, such as the arterial signal 114 in this example, can inadvertently be deposited in 3D voxels representing undesired structures, such as the venous region 120 in this example. The unwanted structures can thus be preserved in the 4D image as "shadow artifacts" when their signal lies along the projected values of a desired structure in a dimension inadequately characterized by the time-series of 2D images. This can result, for example, in a 4D-DSA image in which desired arterial structures are obscured by undesired venous structures for some time frames. However, this will cause a temporary anomaly in the contrast versus time course for the vein. If the time frames of the 4D-DSA image are analyzed, this anomaly can be recognized as inconsistent with the general waveform of the vein and the vein can be suppressed in the time frame where the projected arterial signal is strong. Accordingly, temporal parameters such as mean transit time (MTT) or time-to-fractional-peak can be calculated for each voxel and this information can be used to clean up shadow artifacts. To assist an operator in identifying shadow artifacts and temporal irregularities, the temporal parameters can be color-coded and superimposed on the 4D-DSA image delivered at process block 110 of FIG. 4. The temporal parameters can also be exploited to infer information related to potential perfusion abnormalities in the absence of direct perfusion information from parenchymal signal. Further still and as will be described in detail, velocity information can be used to discern arterial structures or venous structures and distinguish or discriminate between the two.

The acquisition of contrast enhanced image data can be performed following the administration of contrast agent to the subject via either IV or IA injection. When scanning a local area, IA injections allow high image quality and temporal resolution as well as reduced contrast agent dose. However, IV injections are often more suitable for scanning larger regions where multiple IA injections at different locations and different arteries would otherwise be required.

Regardless of whether the contrast agent is introduced as an IV or IA injection, the present disclosure provides systems and methods for utilizing information about the time of arrival (TOA) of the contrast agent to provide flow or velocity data along with the 4D DSA images. Thus, while the above-described process generates time-resolved 3D image or 4D DSA images, as will be described, the above described process can be augmented to provide 4D DSA images with flow or velocity information.

The basic 4D DSA process described above can be augmented to provide the ability for quantification of blood velocity or flow. That is, as will be described, the present disclosure provides systems and methods to incorporate quantitative information into 4D DSA through the development of a TOA display. For example, referring to FIG. 1, the display 18, 20, can show the 4D DSA images where the voxels in each 4D DSA volume are color-coded with the time at which the voxel intensity crosses a preselected fraction of the threshold for that voxel. The color-coded voxel is also modulated by the voxel intensity, thus, reflecting both time and iodine concentration.

Referring to FIG. 3, the above-described 4D DSA process can be augmented to track contrast curves at process block 130. This information, as will be described, will allow the above-described 4D DSA frames to be augmented so that the voxels will reflect both iodine concentration and user selected temporal parameters, such as time of arrival, blood flow velocity, and flow. To do so, at process block 132, the centerline of each vessel in the 3D images is determined. The centerline of the vessels can be found using, as a non-limiting example, a process such as described in Eric Schrauben, Anders Wåhlin, Khalid Ambarki, Jan Malm, Oliver Wieben, and Anders Eklund. Automated 4D Flow Whole Vessel Segmentation and Quantification using Centerline Extraction. ISMRM 2014 abstract, which is incorporated herein by reference in its entirety. Skeletonization on a binary 3D DSA volume can be performed according to, as a non-limiting example, a thinning procedure suitable for elongated objects such as blood vessels, resulting in a one-voxel wide vessel centerline representation.

At process block 134, a TOA curve is generated for each voxel. In one form, a threshold may be compared to the arrival time curve at any position in a vessel. However, such a process is subject to noise. Instead the TOA curve may be calculated by taking the first temporal moment of the contrast curve normalized by an integral over the contrast curve:

$$TOA(x) = \frac{\int C(t, x)t\,dt}{\int C(t, x)dt};\qquad \text{Equation 1}$$

where x is the vector 3D position along the centerline and C is time dependent and spatially dependent contrast curve. Thus, TOA is calculated by using the first moment of the frame time weighted by the contrast arrival curve and normalized by the integral of the contrast arrival curve. This process generates a temporal parameter with good SNR for each voxel reflecting the advancement of the bolus and does so using the statistical information from the entire contrast curve rather than the value at a specific time.

For each point x, the inverse of the slope of TOA vs. x, namely dx/dt provides a local estimate of the average blood speed over the cardiac cycle. Thus, local velocity is calculated as the inverse of the slope calculated.

Figure 6A:
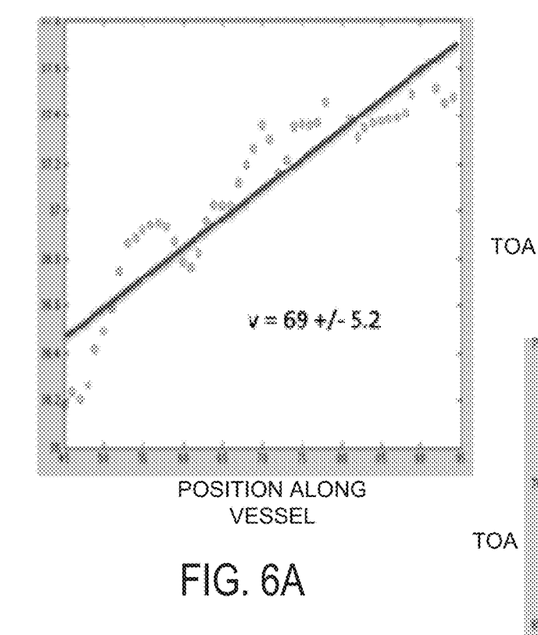
FIG. 6A is a graph showing time of arrival versus vessel position derived in accordance with the present disclosure and illustrating a first flow direction through the vessel.
Figure 6B:
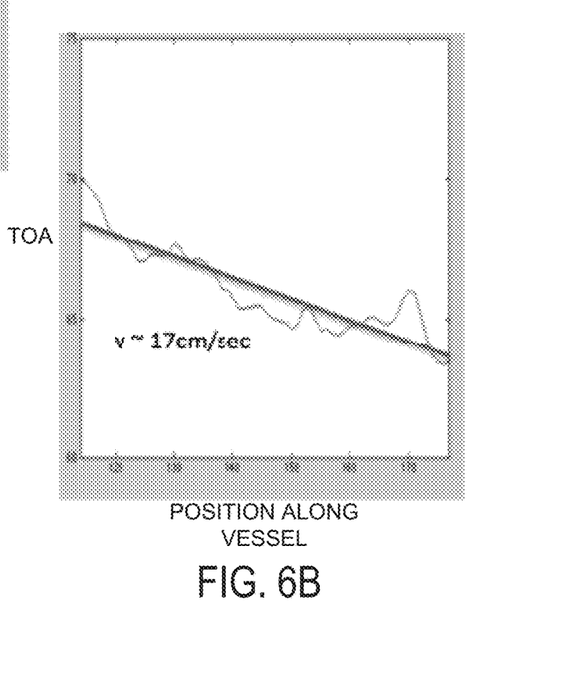
FIG. 6B is a graph showing time of arrival versus vessel position derived in accordance with the present disclosure and illustrating a second flow direction through the vessel.
Figure 6C:
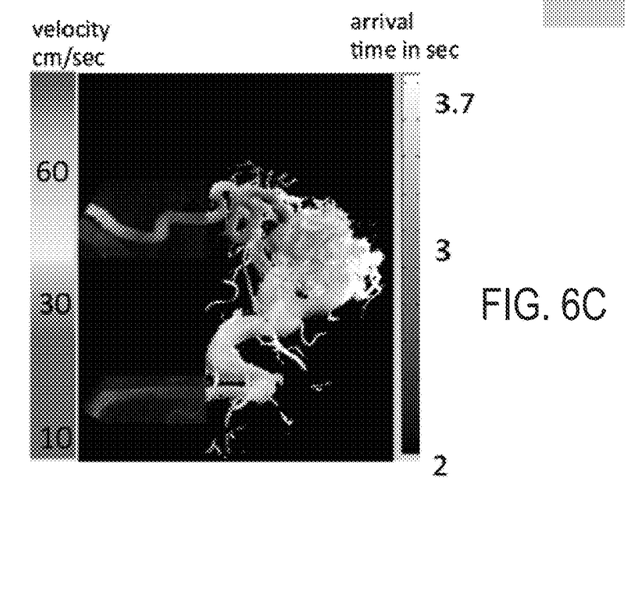
FIG. 6C is an image showing flow velocity and time of arrival in a composite 4D DSA image in accordance with the present disclosure.

Referring to FIGS. 6A and 6B, TOA curves are illustrated. In particular, FIG. 6A illustrates a TOA verses position in an artery and FIG. 6B illustrates TOA versus position in a vein. As illustrated, the gradient of the TOA versus position curve provides velocity. FIG. 6C is a composite image showing a color velocity representation in the artery 131 and vein 133 corresponding to the two graphs 135, 137. The first scale 135 provides a color-coded velocity scale and the second scale 137 provides a grey-scale display of arrival time in the non-color-coded vessels segments 139. Furthermore, the processing can be constrained to a limited or selected region of interest (ROI).

At process block 136, to fit the slope of the TOA values determined by Equation 1, the order of points along a given vessel in which velocity is to be measured may be determined. For example, referring to FIG. 7, a schematic illustration of a vessel 200 is provided. To determine the order of points along the vessel 200 at process block 136 of FIG. 3, a marching cubes algorithm may be used. In doing so, a series of marching cubes 202, 204 are used to find the order and position of points 206 along a centerline 208 of the vessel 200. As a non-limiting example, the vessel 200 may be the carotid artery. Vessel branch endpoints and junction points can be automatically identified and labeled within the vascular tree to produce a unique branch identification for each vessel.

Figure 7:
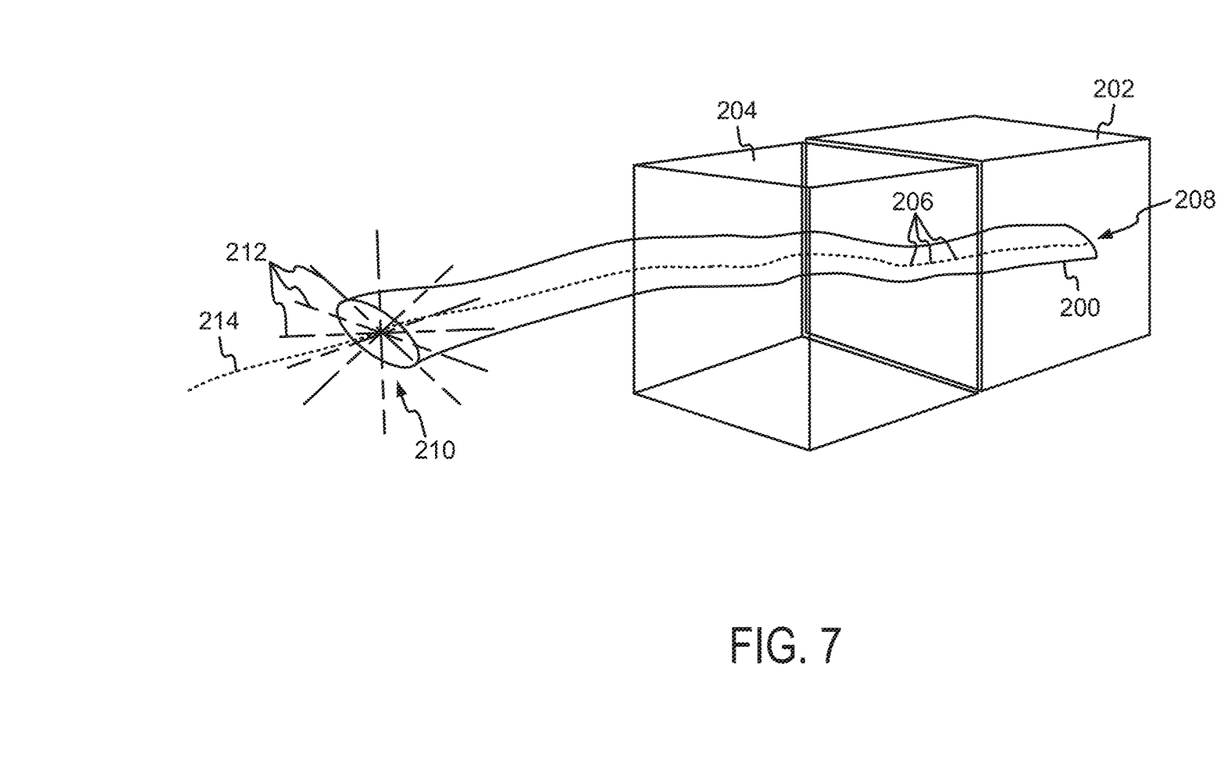
FIG. 7 is a schematic illustration of a centerline and rotating mask strategy for determining vessel direction in accordance with the present disclosure.

Alternatively, a wider range of vessels and associated velocities may be processed automatically using a rotating mask process, which may rotate in 3D, such that the rate of change of TOA values along the centerline 208 can be used to estimate velocity. Alternatively, the complete centerline data may be used to determine the local direction of the centerline 208 in order to calculate the local TOA gradient of the TOA, such as described above with respect to FIGS. 6A and 6B at each point 206. This rotating mask algorithm uses rotating binary masks 210 to determine the direction of the centerline 210 by positioning a plurality of masks 212 along a potential centerline 214 and calculating a probability measure for each pixel that a given mask 212 is aligned with the potential centerline 214. The mask 212 is rotated in 3D to find the orientation that has the highest correlation with the local centerline 208. This process controls against the need to trace the centerline 208 through bifurcations because the rotating mask 212 can be used to automatically track centerlines through bifurcations. Thus, velocity can be calculated at each point 206 in the vascular volume 208 without having to proceed step by step through the vascular tree.

Regardless of the particular algorithm utilized, determining the centerline inside complex structures, such as arteriovenous malformations (AVMs) and aneurysms, can be difficult. Even if the centerline or centerlines of a particular complex structure cannot be adequately determined, the above-described systems and methods can be used to determine centerlines and velocities of the vessels entering and exiting these complex structure. When a region where the determination of the centerline may be unreliable, the above-described systems and methods can insert the grey scale 4D DSA information into the color display or otherwise indicate that the flow information is not available in that complex structure. Nevertheless, the clinician's needs are met by providing the flow information entering and exiting the complex structure.

Referring again to FIG. 3, at process block 138, the derived velocity and/or direction information can be used to generate a velocity volume. The velocity volume may be created using a color lookup table or other memory-storage mechanism. The lookup table or other mechanism may store velocity values or ranges and associated color codings. As such, the derived velocity information can be compared to the color lookup table or other memory-storage mechanism to generate flow/velocity volumes that are color coded. At process block 140, the flow/velocity volume, and associated color information, is combined with the 4D DSA images. More particularly, at process block 140, the volume may be modulated by the 4D DSA intensity values at each point in time. For example, the arrival volume may be subjected to a color preserving multiplication by each of the time resolved 4D DSA time frame volumes. As such, the color-coded voxel is also modulated by the voxel intensity to, thereby, reflect both time and iodine concentration.

Figure 8:
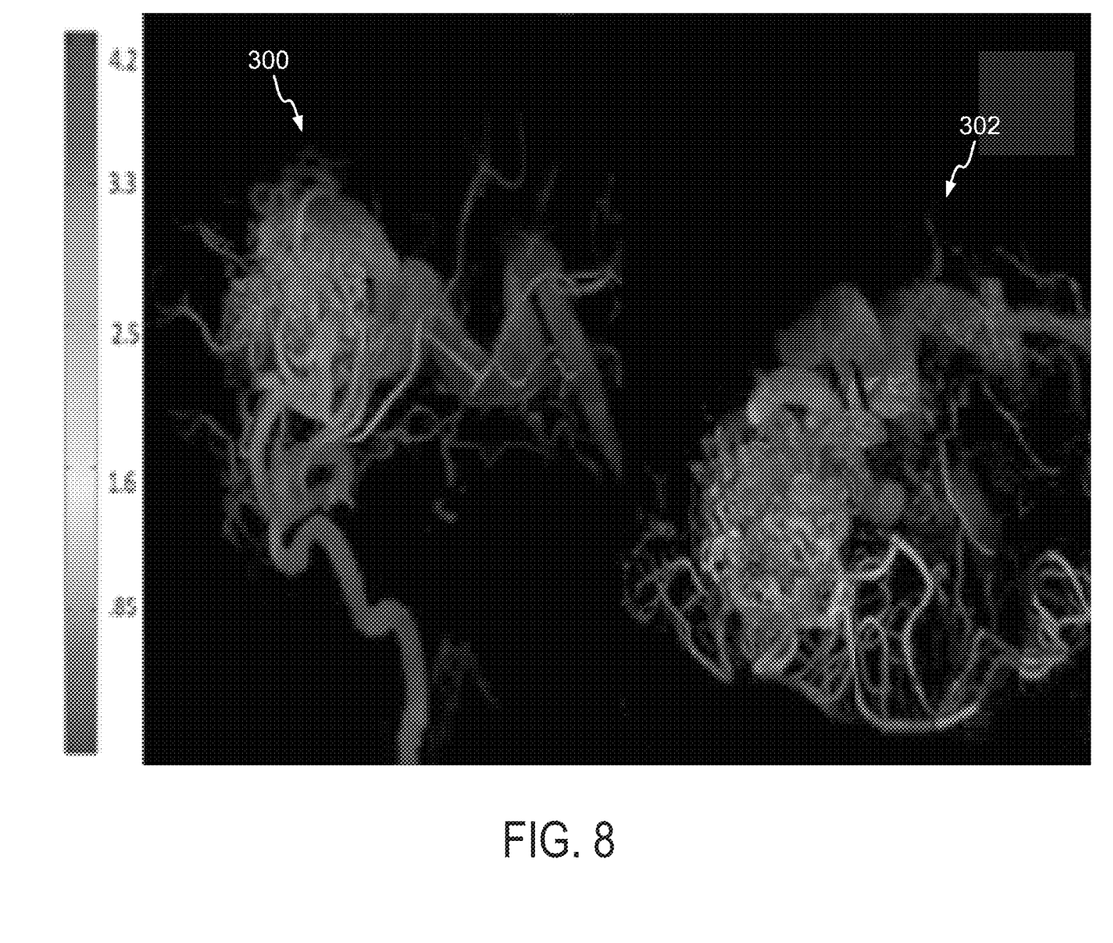
FIG. 8 is an image showing two frames from a movie of a color-coded time of arrival display of a 4D DSA showing an AVM.

An example image is provided in FIG. 8. In particular, FIG. 8 shows two frames 300, 302 from a movie of a color-coded time of arrival display of a 4D DSA showing an AVM. Note that the second frame 302, but for the present disclosure, would have required a dose-prohibitive, x-ray path passing directly from head to foot. This view is available because of the 3D nature of the 4D DSA time frame.

Thus, as described above, systems and methods are provided to obtain quantitative flow information using analysis of 4D-DSA flow curves. The result is the ability to display quantitative information created by providing a color coded display of the 4D DSA frames so that the voxels reflect both iodine concentration and user selected temporal parameters, such as time of arrival, blood flow velocity, and flow.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for generating time: resolved series of angiographic volume data having velocity or velocity-derived information integrated therewith, the system comprising:
an image processing system configured to:
perform an imaging acquisition by receiving angiographic volume data acquired from a subject having received a dose of a contrast agent using an imaging system;

process the angiographic volume data to generate time-resolved, three-dimensional images by:

generating a time-series of two-dimensional images, each of the two-dimensional images corresponding to a different time during the imaging acquisition and a different view angle relative to the subject, wherein each of the two-dimensional images comprises pixel intensity information;

reconstructing a three-dimensional image of the subject without temporal resolution;

determining, for each of a plurality of the two-dimensional images, voxel weightings in the three-dimensional image without temporal resolution using the two-dimensional images; and producing the time-resolved, three-dimensional images of the subject by selectively combining the three-dimensional image without temporal resolution and the time-series of two-dimensional images;

deriving flow information associated with vessels in the time-resolved, three-dimensional images by determining an arrival curve for the contrast agent from the angiographic volume data indicating a rate of change of the a time of arrival (TOA) of contrast agent, wherein the TOA is calculated using a first moment of a frame of the time-resolved, three-dimensional images of the subject weighted by a contrast arrival curve and normalized by an integral of the contrast arrival curve;

modulating at least a portion of the vessels in the time-resolved, three-dimensional images with the flow information; and a display configured to display the time-resolved, three-dimensional images of the subject modulated by the flow information.

2. The system of claim 1 wherein the display is configured to display the flow information as time-resolved, color-coded flow information aligned with at least a portion of the vessels in the time-resolved, three-dimensional images.

3. The system of claim 1 wherein the image processing system is configured to determine a centerline of a given vessel in a region of interest (ROI) in the time-resolved, three-dimensional images and use the centerline to align the flow information with the given vessel in the ROI.

4. The system of claim 3 wherein the image processing system is further configured to determine the TOA of the contrast agent in the given vessel in the ROI.

5. The system of claim 4 wherein the image processing system is further configured to generate a TOA curve for each voxel in the given vessel in the ROI.

6. The system of claim 5 wherein the image processing system is further configured to generate color-coded flow information from the TOA curve for each voxel in the given vessel in the ROI.

7. The system of claim 5 wherein the image processing system is further configured to perform one of a marching cube process and a rotating mask process to determine a flow direction within the given vessel in the ROI.

8. The system of claim 7 wherein the image processing system is further configured to compare the flow direction and the TOA curve for each voxel in the given vessel in the ROI to a lookup table to determine a color coding for each voxel.

9. The system of claim 8 wherein the image processing system is further configured to modulate the color coding for each voxel by a voxel intensity of the time-resolved, three-dimensional images.

10. The system of claim 3 wherein the ROI includes one of a selected portion of the vessels in the time-resolved, three-dimensional images or all vessels in the time-resolved, three-dimensional images.

11. The system of claim 1 wherein the flow information includes at least one of a direction of flow and a velocity.

* * * * *

UNITED STATES PATENT AND TRADEMARK OFFICE
CERTIFICATE OF CORRECTION

PATENT NO. : 10,818,073 B2  
APPLICATION NO. : 14/643853  
DATED : October 27, 2020  
INVENTOR(S) : Charles A. Mistretta et al.

It is certified that error appears in the above-identified patent and that said Letters Patent is hereby corrected as shown below:

In the Claims

Column 11, Claim 1, Line 23, "change of the a time of arrival (TOA) of contrast" should be --change of a time of arrival (TOA) of the contrast--.

Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*